United States Patent [19]

Romaine

[11] 4,377,160

[45] Mar. 22, 1983

[54] COMPRESSION BANDAGE

[76] Inventor: John W. Romaine, 58897 County Rd. 115, Goshen, Ind. 46526

[21] Appl. No.: 218,380

[22] Filed: Dec. 19, 1980

[51] Int. Cl.³ .............................................. A61L 15/00
[52] U.S. Cl. ..................................... 128/156; 128/169
[58] Field of Search ................ 128/169, 156; 428/315, 428/424.2; 515/56; 424/28

[56] References Cited

U.S. PATENT DOCUMENTS

| | | | |
|---|---|---|---|
| 2,185,692 | 1/1940 | McCleary | 219/46 |
| 2,249,537 | 7/1941 | McDowell | 252/316 |
| 3,132,688 | 5/1964 | Nowak | 165/25 |
| 3,175,558 | 3/1965 | Caillouette et al. | 128/403 |
| 3,419,006 | 12/1968 | king | 128/268 |
| 3,463,161 | 8/1969 | Andrassy | 128/402 |
| 3,545,230 | 12/1970 | Morse | 62/530 |
| 3,643,665 | 2/1972 | Caillouette | 128/403 |
| 3,674,134 | 7/1972 | Turner | 206/47 A |
| 3,713,445 | 1/1973 | Marsan | 128/283 |
| 3,780,537 | 12/1973 | Spencer | 62/530 |
| 3,874,504 | 4/1975 | Verakas | 206/219 |
| 3,885,403 | 5/1975 | Spencer | 62/530 |
| 3,998,215 | 6/1976 | Anderson | 128/2.06 E |

FOREIGN PATENT DOCUMENTS 48-8092522  11/1973  Japan .
51-1112511  10/1976  Japan .
53-3050320   5/1978  Japan .

OTHER PUBLICATIONS

Monsanto Technical Bulletin No. 6082D.
Skeist, "Handbook of Adhesives", p 369, 1964.

*Primary Examiner*—Allan Lieberman
*Assistant Examiner*—Patricia Short
*Attorney, Agent, or Firm*—Flynn, Thiel, Boutell & Tanis

[57] ABSTRACT

A self-sticking compressive bandage effective for cooling and compressing an injured body part of a human being or an animal. The bandage comprises a flexible, open-cell, synthetic resin foam impregnated with a hydrous gel. The bandage is effective to cool the skin by evaporative cooling and by refrigeration caused by contact of the gel with the skin.

16 Claims, 3 Drawing Figures

COMPRESSION BANDAGE

FIELD OF THE INVENTION

This invention relates to an improved bandage, and more particularly an improved compression bandage adapted to be wrapped around a selected portion of the human or animal body, for minimizing swelling caused by a sprain, contusion or bruise.

BACKGROUND OF THE INVENTION

Many bodily injuries, particularly those which are commonly referred to under the broad designation of contusions, are painful and cause substantial discomfort to the injured person due to the tissue damage and the resulting hemorrhaging of blood beneath the skin, which in turn causes substantial swelling. Swelling causes the injury to be more painful and disabling. It has long been recognized that, if the swelling can be minimized, then the pain and discomfort can be minimized or eliminated. For this purpose, it has been conventional practice to apply ice packs or similar devices to the injured portion of the body as soon as possible after the injury occurs in an attempt to minimize swelling. This technique, however, is conveniently usable only under specific situations and circumstances. For example, ice packs and the like can be conveniently applied only to certain types of injuries, and use of such ice packs normally does not permit application of proper compression on and around the injured area so as to achieve the best possible minimization of swelling. Further, when an ice pack is applied, the injured person has little freedom of movement.

Accordingly, the present invention relates to an improved bandage for use with injuries of the above type. More specifically, this invention relates to an improved compression bandage which can be quickly and easily wrapped around an injured portion of the body, such as a body part which has suffered a contusion, to minimize subsequent swelling of the body in the region of the injury. This improved bandage not only permits application of proper compression on and around the injured body portion, but also permits cooling of the injured body portion due to both refrigeration and evaporation. This improved bandage also adheres to itself so that it can be easily wrapped around the injured body portion and will securely stay in position without requiring other wraps or ties, so that the injured person thus has substantial freedom of movement even after the bandage is applied. At the same time, the bandage achieves substantially total skin contact to maximize the compression and cooling effects.

In addition, the improved bandage is clean and nontoxic, and does not stick or adhere to the skin so that the bandage can be easily unwrapped from the injured body portion without causing discomfort or requiring any cleaning of the skin. The bandage is also packageable in a small and compact form because it can be spirally rolled for storage. It can be stored in a refrigerator to increase the cooling properties thereof when subsequently applied, it can be readily reused, and it is low in cost.

The improved compression bandage of this invention basically comprises an elongated strip of a gel-like material which is self-supporting and self-adhering, which strip preferably has a thickness of approximately ¼ inch and a width of about 2 inches, with the length of the strip being selected so as to permit the bandage to be wrapped several times around the injured body area, such as around an ankle or wrist. The bandage, when utilized, is wrapped several times around the injured area so that the various convolutions of the bandage overlap and hence adhere to one another so that the bandage will remain in a wrapped condition without requiring additional clips or ties. The gel-like material of the bandage does not adhere or stick to the skin, but it is capable of substantially total surface-to-surface, non-adhering contact with the skin to provide the desired cooling and compressing thereof. The gel-like material permits cooling of the injured body area by evaporation, and the cooling of the injured body area is preferably further assisted by cooling the bandage in a refrigerator prior to application of same to the injured body area.

The gel-like material of the bandage preferably is formed by gelling a polyvinyl alcohol solution formed by using approximately 6 parts or more of polyvinyl alcohol per 100 parts of water. A sheet or strip of thin polyurethane foam is dipped in the polyvinyl alcohol solution, and is thereafter dipped in a reactive gelling agent solution, such as an aqueous borax solution, to form a gel. The polyvinyl alcohol gel also preferably has another ingredient, such as glycerine, incorporated therein so as to make the resulting gel material more pressure-sensitive at lower temperatures, such as at refrigeration temperatures, for example, about 1° to 5° C. The polyurethane foam functions as a central core or carrier for providing the wrap with increased strength and continuity so as thereby to facilitate handling of the bandage and to prevent accidental tearing of the bandage during handling and usage of same.

Other objects and purposes of the invention will be apparent after reading the following specification and inspecting the accompanying drawings.

DETAILED DESCRIPTION OF THE INVENTION

Figure 1:
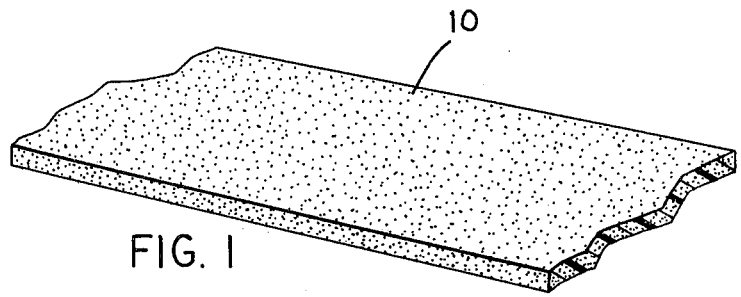
FIG. 1 is a perspective view of a fragment of the bandage.
Figure 2:
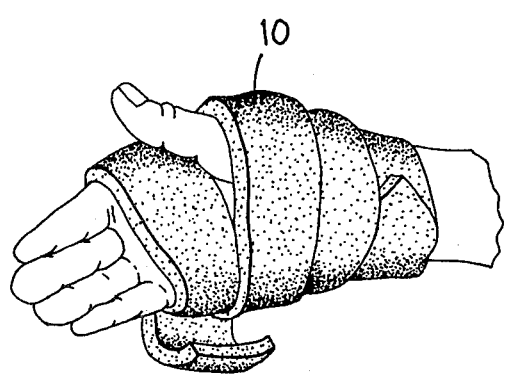
FIG. 2 illustrates one manner of use for the bandage, namely, wrapping of the bandage around an injured hand or wrist.
Figure 3:
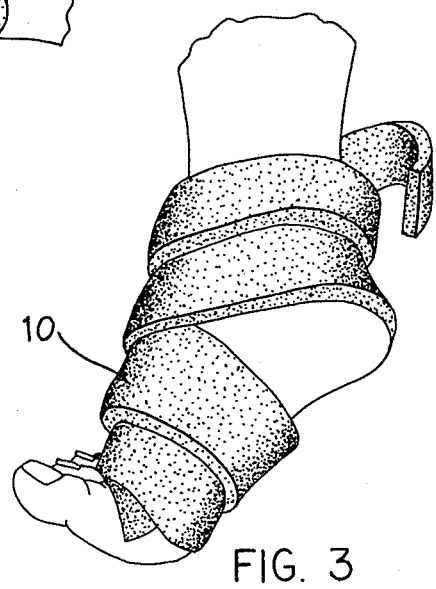
FIG. 3 illustrates another use of the bandage for wrapping same around an injured ankle or foot.

Referring to the drawings, FIG. 1 illustrates a fragment of a compression bandage 10 according to the present invention. The bandage 10 is an elongated, flexible, pliant, flat strip which is adapted to be wrapped around a part of the human or animal body, such as the wrist and hand (FIG. 2) or the foot and ankle (FIG. 3), in order to apply compression on and to cool that body part. The opposite surfaces of the bandage are self-adherent to one another so that the contacting surface portions of the turns or convolutions of the strip releasably adhere to each other whereby the bandage will remain in place on the human or animal body part until it is removed. Although a separately applied adhesive can be applied between the contacting surfaces of the bandage to obtain the above-described adhesion, it is preferred, for convenience in use, to make the opposite surfaces of the bandage self-adherent. It is preferred that the self-adherent properties of the bandage be such that the bond strength at the adhesive joint is less than the strength of the bandage itself in order that removal of the bandage will be achieved by adhesive bond failure at the adhesive joint, rather than cohesive failure of the material of which the bandage is made, in order that the bandage will not be destroyed when it is removed.

The bandage 10 does not significantly adhere to the skin of the human or animal body so that the bandage can easily be removed from the body part by a simple unwrapping or peeling procedure, without causing injury or discomfort to the skin or requiring significant cleaning of the skin.

The bandage 10 preferably is somewhat elastically elongatable so that it can be moderately stretched when it is applied to the body part in order to apply a moderate compression onto the body part around which it is wrapped. For this purpose, the bandage 10 has an elastic elongation of at least about 10 percent and, preferably, in the range of from about 25 to about 75 percent.

The thickness, flexibility and pliability of the bandage 10 are devised so that when the bandage is wrapped around the part of the human or animal body, it will conform closely to the contour of that body part in order that substantially the entire inner surface of the strip will be in surface-to-surface contact with that body part, except for the regions of the strip whereat edge portions of adjacent turns thereof are overlapped with one another. The thickness of the strip is ordinarily in the range of about 3/16 to about 5/16 inch, preferably about ¼ inch. The width of the strip is selected so that the body part can be completely wrapped by making only a few turns of the bandage around the body part. Thus, for wrapping the extremities of the human body, such as the hand or foot, the width of the bandage is from about 1 inch to about 3 inches, preferably about 2 inches. The length of the bandage is selected so as to be effective to wrap the entire area of the human or animal body part to which the bandage is to be applied. For example, the length of the bandage can be from about 2 to about 6 feet, with a length of about 4 feet being preferred for most practical uses.

The bandage 10 is made of a flexible, open-cell, synthetic resin, foam material which is impregnated with a high water content gel, which gel is capable of adhering to itself, but which does not, however, adhere strongly to the human or animal skin. When applied to the skin, the bandage will cool the skin by evaporative cooling. Such cooling effect can be enhanced by refrigerating the bandage 10 in advance. For example, the bandage can be kept in a refrigerator, at about 1° to 5° C., until it is to be used.

Figure 4:
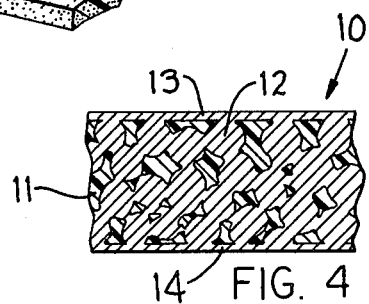
FIG. 4 is a cross section of a fragment of the bandage.

Referring to FIG. 4, the flexible, open-cell, synthetic resin foam material 11 functions as a carrier or a porous substrate for holding the gel 12. The gel 12 penetrates into and substantially completely fills the cells of the foam material 11 and the gel also forms thin integral surface layers 13 and 14 which substantially completely cover the opposite surfaces of the foam material. The gel layers 13 and 14 are self-adherent to each other but they do not strongly adhere to the skin.

It is preferred to use a polyurethane foam as the flexible, open-cell, synthetic resin, foam material 11. Flexible, open-cell, polyurethane foam sheets and strips are commercially available materials. Typically, they have a density of about 0.8 to about 5 pounds per cubic foot, a tensile strength of about 12 to about 150 pounds per square inch and an elongation of about 75 to 150 percent. Flexible, open-cell, polyurethane foams have a high water absorption capability so that they can easily absorb the aqueous solution from which the gel is made.

The gel 12 is obtained by gelling an aqueous solution of polyvinyl alcohol which has previously been impregnated into the foam material 11. The gel 12 is formed, in situ in the foam material 11, by gelling an aqueous solution consisting essentially of about 4 to about 8 weight percent, preferably from about 5 to about 7 weight percent, of polyvinyl alcohol, and the balance is essentially water. It is well known that aqueous solutions of polyvinyl alcohol are coagulated by contacting same with various inorganic and organic compounds. As inorganic compounds, there can be mentioned sodium borate, sodium carbonate, ammonium sulfate, sodium sulfate, potassium sulfate, aluminum sulfate, zinc sulfate, etc. As typical organic compounds capable of coagulating polyvinyl alcohol, there can be mentioned Congo Red, resorcinol, direct azo dyes, etc. It is preferred to use sodium borate (borax) as the agent for gelling the polyvinyl alcohol aqueous solution employed in the invention because sodium borate is capable of rapidly insolubilizing the polyvinyl alcohol by a chemical cross-linking action. For example, treatment of the foam 11 previously impregnated with the polyvinyl alcohol aqueous solution, with an aqueous solution containing from about 2 to about 5 weight percent of sodium borate will rapidly gel the polyvinyl alcohol in order to insolubilize same and to trap or occlude the water therein.

Gellable polyvinyl alcohol solutions can be prepared by dissolving polyvinyl alcohol in water in accordance with conventional practice. Polyvinyl alcohols having various degrees of hydrolysis are commercially available from various manufacturers, for example, Gelvatol polyvinyl alcohols are commercially available from Monsanto and Vinol polyvinyl alcohols are commercially available from Air Products and Chemicals, Inc. The typical commercially available polyvinyl alcohols have a degree of polymerization of from about 300 to about 2,000 and a degree of hydrolysis (%) of about 88 to about 100 percent.

It is preferred to use a mixture of polyvinyl alcohols having different degrees of hydrolysis in order to prepare the gel, according to the invention. For example, it is preferred to use a mixture of (1) from 20 to 30 wt. %, preferably about 25 wt. %, of polyvinyl alcohol having a degree of hydrolysis of 98% or more, and correspondingly (2) from 80 to 70 wt. %, preferably about 75 wt. %, of polyvinyl alcohol having a degree of hydrolysis of from about 87 to 90%. The use of such a mixture is advantageous because it provides a commercially satisfactorily rapid rate of gel formation and it prevents exudation of water from the gel.

The bandage 10 can be easily prepared by immersing the foam material 11 into a bath of an aqueous solution of polyvinyl alcohol so that the foam material becomes substantially completely impregnated with the aqueous polyvinyl alcohol solution and forms the thin surface layers 13 and 14 thereon. Then the impregnated foam material is dipped in an aqueous solution of the coagulating agent, such as sodium borate, so as to transform the polyvinyl alcohol solution into a gel throughout the foam material 11 and surface layers 13 and 14.

In order to improve the self-adhering, pressure-sensitive characteristics of the gel 12, in the bandage according to the present invention, particularly in the surface layers 13 and 14 thereof, it is very advantageous to plasticize at least those surface layers by incorporating a plasticizing material therein. Inasmuch as the self-adhering, pressure-sensitive properties are essentially needed only for the surface layers 13 and 14 and such plasticization is not required in the portions of the gel contained within the body of the foam material 11, it will be sufficient to incorporate a plasticizer in the gelling agent aqueous solution so that the plasticizer migrates into and plasticizes at least the surface layers 13 and 14 of the gel as the gel is formed in situ on the foam material. As the plasticizer, it is preferred to use glycerol because of its high compatibility with polyvinyl alcohol and its effectiveness in imparting a pressure-sensitive property to the polyvinyl alcohol gel. Moreover, because of its relatively high boiling point and low volatility, glycerol is an effective material for practical use. The glycerol prevents the polyvinyl alcohol from becoming hard and brittle at low humidities. Further, the presence of the glycerol improves the tensile elongation of the surface layers 13 and 14. It is effective to incorporate from about 2 to about 10 percent, preferably about 5 percent of glycerol, in the aqueous gelling agent solution that is used to gel the aqueous polyvinyl alcohol solution. If desired, an effective amount of a compatible antiseptic can be incorporated in the gel to prevent deterioration of the gel by microorganisms. An iodine-type antiseptic, such as Amical No. 48 (Abbott Laboratories) is preferred.

The following example will serve to illustrate the preparation of a typical compression bandage according to the present invention.

EXAMPLE

A roll of a strip of flexible, open-cell, polyurethane resin foam was led through a bath of an aqueous solution consisting essentially of 100 parts by weight of water, in which were dissolved 6.5 parts by weight of polyvinyl alcohol, about 0.01 parts by weight of a defoaming agent and about 0.1% of Amical No. 48 (Abbott Laboratories) antiseptic, so that the solution completely impregnated the strip. The polyvinyl alcohol was a mixture of (1) 25 wt. % of Vinol 125 (Air Products and Chemicals, Inc.) having a degree of hydrolysis of 99.6%, and (2) 75 wt. % of Vinol 523 (Air Products and Chemicals, Inc.) having a degree of hydrolysis of 87 to 89%. After impregnation was completed, the impregnated foam strip was then immersed in a second bath of an aqueous solution consisting essentially of 100 parts by weight of water, in which were dissolved 5.0 parts by weight of glycerol and 5 parts by weight of borax. The polyvinyl alcohol solution gelled within a very short time, typically within about 2 minutes or so, following which the foam strip containing the gel was removed from the second bath. The impregnated strip was then hung in a more or less vertical position to allow excess gelled polyvinyl alcohol to drain off. Then the strip was wound up in the form of a roll and was packaged for shipment.

The bandage 10 preferably is stored in a refrigerator at about 5° C. until it is used. However, it is possible to store the bandage without refrigeration if desired. In use the bandage is wrapped around the injured body part and the end of the bandage is lapped over and pressed against one or more of the convolutions thereof to releasably secure the bandage in place. In applying the bandage, the bandage can be elastically elongated so that it will apply moderate pressure on the injured body part. The bandage can be easily removed when the injured person is to receive medical treatment for the injury.

The bandage according to the present invention is non-irritating to the skin, non-toxic, pressure-sensitive and self-sticking. It is capable of achieving good surface-to-surface contact with the skin to apply compression thereon and to cool the injured body part. The bandage is low in cost.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A compression bandage for minimizing swelling caused by contusion of a body part of a human or animal subject, comprising: an elongated, flexible, self-supporting, self-adhereable strip adapted to be wound around the body part in direct surface-to-surface contact with the skin in order to form a multiple convolution compression bandage for compressing the body part and cooling same, said strip being of a length sufficient to permit the bandage to be wrapped totally around the body part with the adjacent convolutions of the bandage being overlapped and adhered to one another so that the bandage will remain wrapped around the body part, said strip consisting essentially of an elongated, thin, substantially planar, flexible, permeable substrate which is impregnated and filled with a gel, said gel consisting essentially of gelled polyvinyl alcohol containing occluded water so that the gel is substantially self-supporting and has a solidlike consistency, said gel being formed by impregnating said substrate with an aqueous solution containing from about 4 to 8 weight percent of polyvinyl alcohol and the balance being essentially water, said polyvinyl alcohol being coagulated with a coagulating agent to insolubilize said polyvinyl alcohol and trap the water therein, said gel being capable of adhering to itself and not being capable of adhering strongly to the skin of the subject, said gel extending to the opposite surfaces of said substrate so that said strip is pressure-sensitive and will adhere to itself and said gel does not strongly adhere to the surface of the skin of the body part so that said strip can easily be unwound and removed from the body part without leaving a significant amount of residue thereon.

2. A bandage as claimed in claim 1 in which said substrate is made of a synthetic resin.

3. A bandage as claimed in claim 1 in which said substrate is an open-cell, synthetic resin foam, the intercommunicating open cells of said foam being substantially filled with said gel.

4. A bandage as claimed in claim 3 in which said synthetic resin foam is a polyurethane foam.

5. A bandage as claimed in claim 1 in which said bandage is non-toxic and non-medicated.

6. A bandage as claimed in claim 5 in which said gel contains a plasticizer in an amount effective to increase the tack thereof.

7. A bandage as claimed in claim 6 in which said plasticizer is glycerol.

8. A bandage as claimed in claim 1 in which said strip has a thickness of from about 3/16 inch to about 5/16 inch, a width of from about 1 inch to about 3 inches and a length of from about 2 feet to about 6 feet.

9. A bandage as claimed in claim 8 in which said bandage has an elastic elongation of from about 25 to about 75 percent.

10. A bandage as claimed in claim 1 or claim 8 in which said bandage has an elastic elongation of at least about 10 percent.

11. A bandage as claimed in claim 1 in which the bandage is free of counter-irritants and analgesics.

12. A bandage as claimed in claim 1 in which said coagulating agent is borax.

13. A bandage as claimed in claim 1 in which said solution contains from about 5 to about 7 weight percent of polyvinyl alcohol.

14. A bandage as claimed in claim 1 in which said polyvinyl alcohol consists of a mixture of (1) from 20 to 30 weight percent of polyvinyl alcohol having a degree of hydrolysis of at least about 98%, and correspondingly (2) from 80 to 70 weight percent of polyvinyl alcohol having a degree of hydrolysis of from about 87 to about 90%.

15. A method of preventing swelling caused by a contusion of the human or animal body which comprises wrapping around the contused body part a compression bandage as claimed in claim 1 to effect cooling of the body part at least partially by evaporation.

16. A method as claimed in claim 15 in which said compression bandage is cooled in a refrigerator before it is wrapped around the contused area.

* * * * *